(12) United States Patent
Johnson et al.

(10) Patent No.: US 7,070,938 B2
(45) Date of Patent: Jul. 4, 2006

(54) METHOD TO DETECT MODULATORS OF VEGF KINASE DOMAIN

(75) Inventors: Dana L. Johnson, Upper Black Eddy, PA (US); Stuart L. Emanuel, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 638 days.

(21) Appl. No.: 09/875,644

(22) Filed: Jun. 6, 2001

(65) Prior Publication Data

US 2002/0037537 A1 Mar. 28, 2002

Related U.S. Application Data

(60) Provisional application No. 60/210,132, filed on Jun. 7, 2000.

(51) Int. Cl.
*G01N 33/53* (2006.01)

(52) U.S. Cl. .................. 435/7.1; 530/350; 435/7.6; 435/7.92

(58) Field of Classification Search .............. 435/7.1, 435/7.5, 7.92, 15; 530/350
See application file for complete search history.

(56) References Cited

U.S. PATENT DOCUMENTS

| | | |
|---|---|---|
| 4,568,649 A | 2/1986 | Bertoglio-Matte |
| 5,283,354 A | 2/1994 | Lemischka |
| 5,770,176 A | 6/1998 | Nargessi |
| 5,861,301 A | 1/1999 | Terman et al. |

FOREIGN PATENT DOCUMENTS

WO    WO 98/58053    12/1998

OTHER PUBLICATIONS

Cook, Neil D. "Scintillation proximity assay: a versatile high-throughput screening technology", *Drug Discovery Today* (1996) 1:287-294.
Wen, Y. et al., "Two Functional Forms of Vascular Endothelial Growth Factor Receptor-2/Flk-1 mRNA are Expressed in Normal Rat Retina", *J. Biol. Chem.* (1998) 273:2090-2097.
Nayakayama, G.R. et al., "A Scintillating Microplate Assay for the Assessment of Protein Kinase Activity", *J. Biomolecular Screening* (1998) 3:43-48.
McDonald, O.B. et al., "A Scintillation Proximity Assay for the Raf/MEK/ERK Kinase Cascade: High-Throughput Screening and Identification of Selective Enzyme Inhibitors", *Anal. Biochem.* (1999) 268:318-329.
Picardo, M. and Hughes, K.T., "Scintillation Proximity Assay: Chapter 16", In *High Throughput Screening* (1997) [Devlin, J.P. (Ed.) Dekker, New York, New York] pp. 307-316.
Parast et al., "Characterization and Kinetic Mechanism of Catalytic Domain of Human Vascular Endothelial Growth Factor Receptor-2 Tyrosine Kinase (VEGFR2 TK), a Key Enzyme in Angiogenesis", *Biochemistry* (1998) 37:16788-16801.
Dougher-Vermazen et al., "Biological Activity and Phosphorylation Sites of the Bacterially Expressed Cytosolic Domain of the KDR VEGF-Receptor", *Biochem. Biophys. Res. Comm.* (1994) 205(1):728-738.
T. Takahashi and M. Shibuya, "The 230 kDa Mature Form of KDR/Flk-1 (VEGF Receptor-2) Activates the PLC-γ Pathway and Partially Induces Mitotic Signals in NIH3T3 Fibroblasts", *Oncogene* (1997) 14:2079-2089.

*Primary Examiner*—Ruixiang Li
*Assistant Examiner*—Dong Jiang

(57) ABSTRACT

The present invention relates to assays for the detection of compounds with pharmacological activity, particularly for the detection of modulators of rat vascular endothelial growth factor receptor (rat VEGF-R2) kinase domain.

2 Claims, 5 Drawing Sheets

Antiphosphotyrosine
Blot of Rat VEGF-R2 Kinase Domain

Lane 1. VEGF-R2, 20 μg
2. VEGF-R2, 10 μg
3. VEGF-R2, 5 μg
4. VEGF-R2, 2 μg
5. VEGF-R2, 1 μg
M. MW Marker (150-, 100-, 75-, 50-, 35-, 25-, and 15-kDa)

INHIBITOR A

Rat VEGF-R2 Assay
IC50 Determination

- Inhibitor-A
  PLC1 substrate
  IC50 = 44 nM

- Inhibitor-A
  PolyGT substrate
  IC50 = 80 nM

Linearity of VEGF-R Kinase Assay
Reaction was allowed to proceed for 1-3.5 hours and the maximum signal vs. time was plotted.

SEQUENCE LISTING

<160> NUMBER OF SEQ ID NOS: 3

<210> SEQ ID NO 1
<211> LENGTH: 28
<212> TYPE: DNA
<213> ORGANISM: Artificial Sequence -continued

```
<220> FEATURE:
<223> OTHER INFORMATION: Description of Artificial Sequence:
      oligonucleotide

<400> SEQUENCE: 1
atcctaggta ccgttatgcg ggccaatg                                              28

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
tgtggcggcc gccgggtggt ggaaag                                                26

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: synthetic
      peptide substrate

<400> SEQUENCE: 3

Lys His Lys Lys Leu Ala Glu Gly Ser Ala Tyr Glu Glu Val
 1               5                  10
```

METHOD TO DETECT MODULATORS OF VEGF KINASE DOMAIN

CROSS-REFERENCE TO RELATED APPLICATION

This application claims the benefit of U.S. Provisional Application Ser. No. 60/210,132, filed Jun. 7, 2000.

BACKGROUND OF THE INVENTION

1. Field of the Invention

The present invention relates to assays for the detection of compounds with pharmacological activity, particularly for the detection of modulators of vascular endothelial growth factor receptor (VEGF-R2) kinase domain.

2. Background

Angiogenesis plays a role in various processes including development of the vasculature, wound healing and maintenance of the female reproductive system. Pathological angiogenesis is associated with disease states such as cancer, diabetic retinopathy, rheumatoid arthritis, endometriosis and psoriasis. The vascular endothelial growth factors (VEGFs) are mediators of both normal and pathologic angiogenesis. VEGF transmits signals into cells through their cognate receptors, which belong to the receptor tyrosine kinase (RTK) family of transmembrane receptors. These receptors are tripartite, consisting of an extracellular ligand-binding domain, a transmembrane domain, which anchors the receptor in the membrane of the cell, and an intracellular tyrosine kinase domain. One subfamily of RTKs comprises the receptors Flt1/VEGF-R1 and KDR/Flk1/VEGF-R2, which bind VEGFs. Binding of the VEGF ligand to the receptor results in stimulation of the receptor tyrosine kinase activity and transduction of biological signals into the cell. The KDR/Flk1/VEGF-R2 receptor mediates the biological activities of mitogenesis and proliferation of endothelial cells while the Flt1/VEGF-R1 receptor mediates functions such as endothelial cell adhesion. Inhibition of KDR/Flk1/VEGF-R2 signalling has been shown to inhibit the process of angiogenesis. Inhibitors of this receptor would be useful in the treatment of diseases where deregulated or uncontrolled angiogenesis exists.

The sequence for the mouse form of VEGF-R2 is described in U.S. Pat. No. 5,283,354. The human sequence is described in U.S. Pat. No. 5,861,301, however, the sequence disclosed in this patent contains several differences from the correct sequence including an inactivating point mutation which renders the protein nonfunctional in the kinase domain. The functional human VEGF-R2 sequence is described in a separate international patent application PCT WO 98/58053. The rat VEGF receptor kinase domain is similar to the corresponding human sequence and was submitted into the public domain on Mar. 13, 1997 (Genbank accession numbers U93306 and U93307) and later described in *J. Biol. Chem.* 273: 2090–97 (1998). The rat intracellular kinase domain is 97% identical to the human sequence in the N-terminal and C-terminal tyrosine kinase regions, and 89% identical in the intervening Kinase Insert Domain (KID). There is no description of a soluble form of the rat VEGF-R2 kinase domain or the use of such a protein in a method to test compounds for suspected kinase inhibitory activity.

Using scintillation proximity technology, homogeneous assays have been developed for a variety of molecular targets (Cook, N. D. (1996). *Drug Discovery Today* 1:287–294; Picardo, M. and Hughes, K. T. (1997). In High Throughput Screening [Devlin, J. P. (Ed)], Dekker, New York, N.Y., pp. 307–316). Briefly, the target of interest is immobilized either by coating or incorporation on a solid support that contains a fluorescent material. A radioactive molecule, brought in close proximity to the solid phase by associating with the immobilized target, causes the fluorescent material to become excited and emit visible light. Emission of visible light forms the basis of detection of successful ligand/target interaction, and is measured by an appropriate monitoring device. An example of a scintillation proximity assay is disclosed in U.S. Pat. No. 4,568,649, issued Feb. 4, 1986. U.S. Pat. No. 5,770,176 describes assays for nuclear receptors wherein the functional receptor binds to immobilized nucleic acid. Materials for these types of assays are commercially available from DuPont NEN® (Boston, Mass.) under the trade name FlashPlate™. Development of scintillation proximity assays for the detection of kinase function has been described for purified src tyrosine kinases to peptide substrates (Naykayama, G. R. et al J. Biomolecular Screening (1998) 3:43–48; McDonald, O. B. et al (1999). Anal. Biochem. 268:318–329.) To our knowledge, there are no reported scintillation proximity assays describing soluble VEGF tyrosine kinase function or testing inhibitory compounds using similar techniques.

SUMMARY OF THE INVENTION

The present invention provides methods to measure phosphorylation by a fusion protein comprising the rat VEGF kinase domain and assays to detect modulators of VEGF kinase activity.

Thus the invention provides a method and assay for the detection of compounds that modulate VEGF kinase enzymatic activity comprising the steps of:

A) providing a test compound, a rat VEGF-R2 kinase fusion protein, and a kinase substrate comprising an affinity moiety and a rat VEGF-R2 phosphorylation site in a solution suitable to provide rat VEGF-R2 catalytic activity and containing $^{33}$P-γ-ATP as the source of phosphate;

B) contacting the compound, kinase fusion protein, and kinase substrate for sufficient time to provide a $^{33}$P phosphorylated substrate;

C) isolating the phosphorylated kinase substrate by affinity capture in a multiwell assay plate;

D) removing remaining $^{33}$P-γ-ATP by first aspirating the aqueous solution and then washing with plate with a second solution; and E) detecting a change in kinase activity by monitoring the rate or absolute amount of $^{33}$P transfer by the kinase to the substrate in the presence of the compound.

DETAILED DESCRIPTION

Figure 1:
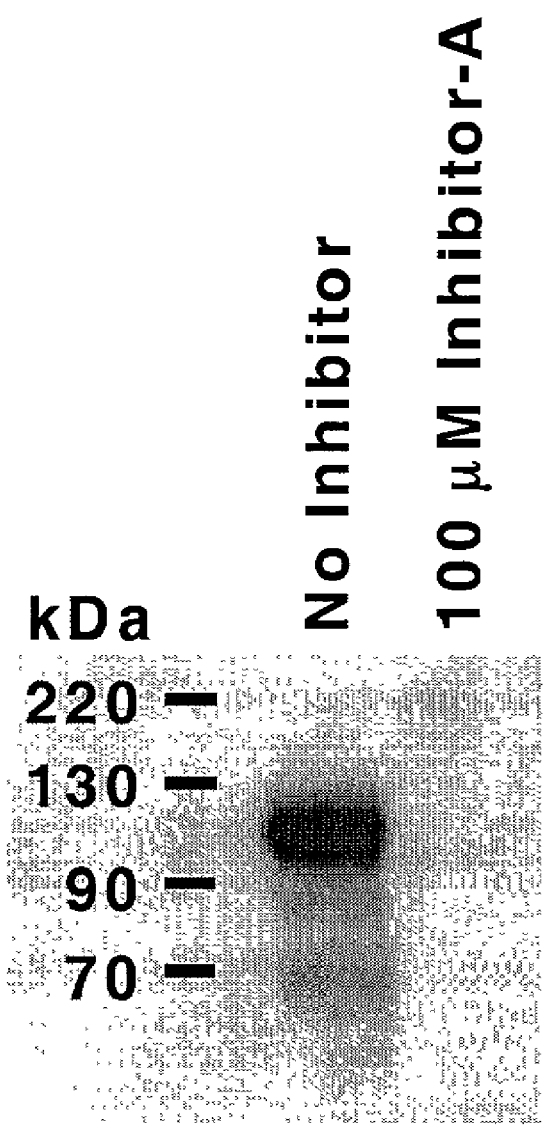
FIG. 1: Western Blot: anti-Phosphotyrosine of Rat VEGF-R2 Kinase Domain +/− an inhibitor

Definitions:

The term "protein domain" as used herein refers to a region of a protein that can fold into a stable three-dimensional structure, often independently of the rest of the protein, and which is endowed with a particular function. This structure may maintain a specific function associated with the domain's function within the original protein including enzymatic activity, creation of a recognition motif for another molecule, or provide necessary structural components for a protein to exist in a particular environment of proteins, both within a protein family and within related protein superfamilies protein domains can be evolutionarily conserved regions.

The term "protein superfamily" as used herein refers to sets of proteins whose evolutionary relationship may not be entirely established or may be distant by accepted phylogenetic standards, but show similar three dimensional structure or display unique consensus of critical amino acids. The term "protein family" as used herein refers to proteins whose evolutionary relationship has been established by accepted phylogenic standards.

The term "fusion protein" as used herein refers to a novel chimeric protein construct that is the result of combining two or more domains or linker regions from different proteins for the purpose of combining in one single polypeptide chain functions and recognition properties normally associated with two or more distinct polypeptides. This is most often accomplished by the adjacent molecular cloning of the nucleotide sequences encoding for the desired protein domains to result in the creation of a new polynucleotide sequence that codes for the desired protein. Alternatively, creation of a fusion protein may be accomplished by chemically joining two proteins together.

The term "linker region" or "linker domain" or similar such descriptive terms as used herein refers to stretches of polynucleotide or polypeptide sequence that are used in the construction of a cloning vector or fusion protein. Functions of a linker region can include introduction of cloning sites into the nucleotide sequence, introduction of a flexible component or space-creating region between two protein domains, or creation of an affinity tag for specific molecule interaction. A linker region may be introduced into a fusion protein without a specific purpose, but as a compromise that results from choices made during cloning.

The term "cloning site" or "polycloning site" as used herein refers to a region of the nucleotide sequence contained within a cloning vector or engineered within a fusion protein that has one or more available restriction endonuclease recognition sequences. Adequate manipulation of restriction endonuclease sites allows to clone in tandem two or more nucleotide sequences so that the respective encoded protein domains are translated in frame relative to a particular start codon, thus yielding a desired protein product after transcription and translation. These nucleotide sequences can then be introduced into other cloning vectors, used to create novel fusion proteins, or used to introduce specific site-directed mutations. It is well known by those in the art that cloning sites can be engineered at a desired location by silent mutations, conserved mutation, or introduction of a linker region that contains desired restriction enzyme consensus sequences. It is also well known by those in the art that the precise location of a cloning site can be flexible so long as the desired function of the protein or fragment thereof being cloned is maintained.

As used herein, "expression vectors" are defined herein as nucleic acid sequences that are required for the transcription of cloned copies of genes and the translation of their mRNAs in an appropriate host. Such vectors can be used to express eukaryotic or prokaryotic genes in a variety of hosts including *E. coli*, blue-green algae, plant cells, insect cells, fungal cells including yeast cells, and animal cells.

The term "test compound" as used herein in connection with a suspected modulator of VEGF-R kinase activity refers to an organic molecule that has the potential to disrupt the specific enzymatic activity of the kinase. For example, but not to limit the scope of the current invention, compounds may include small organic molecules, synthetic or natural amino acid peptides, proteins, or synthetic or natural nucleic acid sequences, or any chemical derivatives of the aforementioned. Compounds that are agonists increase the rate or total amount of phosphate transferred to the kinase substrate. Compounds that are antagonists decrease the rate or total amount of phosphate transferred to the kinase substrate.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

The present invention provides methods to measure phosphorylation by a fusion protein comprising the rat VEGF kinases domain and assays to detect modulators of VEGF kinase activity. Particularly, fusion proteins useful in the method of the present invention comprise amino acids carboxyl terminal of the transmembrane domain of the rat VEGF-R2 and optionally an affinity tag, for example a polyhistidine tag. A particularly preferred fusion protein is one where a polyhistidine tag is located at the N-terminus and the rat VEGF-R2 kinase domain comprises amino acids 786–1343 of the rat VEGF-R2 protein (SEQ ID NO:4).

Thus the invention provides a method and assay for the detection of compounds that modulate VEGF kinase enzymatic activity comprising the steps of:

A) providing a test compound, a rat VEGF-R2 kinase fusion protein, and a kinase substrate comprising an affinity moiety and a rat VEGF-R2 phosphorylation site in a solution suitable to provide rat VEGF-R2 catalytic activity and containing $^{33}$P-γ-ATP as the source of phosphate;

B) contacting the compound, kinase fusion protein, and kinase substrate for sufficient time to provide a $^{33}$P phosphorylated substrate;

C) isolating the phosphorylated kinase substrate by affinity capture in a multiwell assay plate;

D) removing remaining $^{33}$P-γ-ATP by first aspirating the aqueous solution and then washing with plate with a second solution; and E) detecting a change in kinase activity by monitoring the rate or absolute amount of $^{33}$P transfer by the kinase to the substrate in the presence of the compound.

Rat VEGF-R2 substrates useful in the methods of the present invention are determined by incubating the fusion proteins of the present invention in a suitable buffer with a putative substrate for sufficient time for rat VEGF-R2 enzymatic activity to phosphorylate the substrate. The substrate is isolated, for example by SDS-PAGE, mass spectroscopy, HPLC, or assays described herein and analyzed to determine the presence of phosphate transfer to a tyrosine residue in the substrate. Preferred substrates are the VEGF-R2 kinase domain (via autophosphorylation) polypeptide fragments of rat VEGF-R2, polypeptide fragments of phospholipase C γ, or polyglutamate/tyrosine (Glu:Tyr 4:1).

The assays described herein detect enzymatic activity (and modulation of enzymatic activity) by way of immobilizing the substrate peptide, for instance by use of an affinity moiety—affinity capture pair such as streptavidin capture of a biotinylated substrate peptide. Affinity capture pairs are well known in the art and include, for example, avidin/biotin, antibody epitopes contained within the substrate peptide or larger polypeptide, dextran/maltose binding domain of the *Escherichia coli* malE gene, glutathione S-transferase (GST), and polyhistidine/immobilized nickel. Polyhistidine refers to a polypeptide containing 3 to 10 consecutive histidine residues, particularly six consecutive histidine residues.

Particular affinity capture assays of the invention are termed "Autophosphorylation Assay" and "Polypeptide phosphorylation Assay". In the Autophosphorylation Assay a fusion protein, containing a rat VEGF-R2 kinase catalytic domain and at least one affinity capture domain, is incubated in a buffer suitable for its enzymatic activity in the presence of radiolabeled ATP. The kinase protein autophosphorylates (via one kinase molecule interacting with a similar molecule) resulting in the transfer of a radiolabeled phosphate group to the fusion protein. Then the fusion protein binds to the surface of the scintillation proximity vehicle through a matched affinity capture pair. The phosphorylation is measured by emission of visible light from a scintillation proximity vehicle. In the Polypeptide phosphorylation Assay, a rat VEGF-R2 substrate peptide or polypeptide containing a phosphorylation domain and at least one affinity capture domain is incubated in a buffer suitable for the matching kinase's enzymatic activity in the presence of radiolabeled ATP. The matched kinase protein is added to the mixture and phosphorylates the substrate, resulting in the transfer of a radiolabeled phosphate group to the substrate. Then the phosphorylated substrate binds to the surface of a scintillation proximity vehicle through a matched affinity capture pair. The rat VEGF-R2 kinase protein cannot contain a domain of the affinity capture pair, in order to avoid detecting autophosphorylation. The phosphorylation is measured by emission of visible light from the scintillation proximity vehicle. In both of these cases, the affinity domain may be the existing polypeptide or may be a distinct domain or small peptide introduced as part of a fusion protein.

The preferred method to detect enzymatic activity upon the substrate peptide is to transfer $^{33}P$ to the substrate by hydrolysis of $^{33}P$-γ-ATP. This method comprises the steps, in order;

1) providing a test compound, a rat VEGF kinase fusion protein, and a kinase substrate peptide comprising an affinity moiety and a rat VEGF-R2 phosphorylation site in a solution suitable to provide rat VEGF catalytic activity and containing $^{33}P$-γ-ATP as the source of phosphate;
2) contacting the compound, kinase fusion protein, and kinase substrate for sufficient time to provide a $^{33}P$ phosphorylated substrate;
3) isolating the phosphorylated kinase substrate by affinity capture in a multiwell assay plate;
4) removing remaining $^{33}P$-γ-ATP by first aspirating the aqueous solution and then washing with plate with a second solution;
5) detecting a change in kinase activity by monitoring the rate or absolute amount of $^{33}P$ transfer by the kinase to the substrate in the presence of the compound.

The preferred autophosphorylation method to measure the effect of a putative VEGF-R2 modulating compound upon the kinase activity of rat VEGF-R2 comprises the steps, in order:

A) providing a test compound, a rat VBGF-R2 kinase fusion protein comprising N-terminal hexahistidine linked to amino acids 786–1343 of the rat VEGF-R2 protein (SEQ ID NO:4) in a solution suitable to provide rat VEGF-R2 catalytic activity and containing $^{33}P$-γ-ATP as the source of phosphate;
B) contacting the compound and the kinase fusion protein for sufficient time to provide a $^{33}P$ phosphorylated substrate;
C) isolating the phosphorylated kinase fusion protein by affinity capture using an NTA-Nickel coated multiwell assay plate;
D) removing remaining $^{33}P$-γ-ATP by first aspirating the aqueous solution and then washing the plate with a phosphate buffered saline solution containing a divalent cation chelator in the concentration of about 1 mM to 100 mM; and
E) detecting a change in kinase activity by monitoring the rate or absolute amount of $^{33}P$ transfer to the kinase fusion protein by autophosphorylation in the presence of the compound.

The change in the quantity of product can be total amount as a function of time (a stop-time assay) or can be kinetic by measuring a change in the enzymatic rate as a function of time. Kinetic assays are measured from the time of initial contact of the enzyme and substrate to a point in time where 50% of the maximum observed product is generated.

The amount of expected rat VEGF-R2 enzymatic function can be determined by running, concurrently or separately, an assay as described with a compound that does not inhibit enzymatic function, or with a solvent vehicle that contains a similar properties as that used for the test compound but lacks any test compound, such as DMSO, DMF, or isopropyl alcohol.

The solution used to wash the plate is not particularly limiting, and includes physiologically buffered solutions with or without detergents. These solutions are well known in the art. Particularly preferred solutions contain divalent cation chelator, preferably EDTA or EGTA at a concentration at about 1 mM to about 100 mM. The chelator serves to inhibit further kinase catalytic activity, and increases the assay performance by increasing the signal to noise ratio.

The following examples illustrate the present invention without, however, limiting the same thereto.

EXAMPLE 1

The rat VEGF receptor tyrosine kinase domain was cloned from rat liver cDNA by PCR. The forward primer (5-ATCCTAGGTACCGTTATGCGGGC CAATG: SEQ.ID.No.:1) was designed to correspond with the human VEGF-R2 sequence, but introduced a KpnI site to facilitate subcloning and an artificial start codon that would correspond with amino acid 786 of the rat protein. The reverse primer (5-TGTGGCGGCCGCCGGGTGGTG GAAAG: SEQ.ID.No.:2) corresponded to the mouse VEGF-R2 sequence and introduced a NotI site after the stop codon of the rat gene to facilitate subcloning. This nucleic acid fragment was cloned into the pcDNA3.1(+) expression vector (In Vitrogen Co., Carlsbad, Calif.). The clone was expressed in COS cells and found to be functional in autophosphorylation studies. Experiments with a known inhibitor of VEGF receptor phosphorylation, showed the rat VEGF receptor clone to be inhibited by this compound, thus indicating that the rat VEGF receptor kinase domain functioned in an analogous fashion to similar VEGF-R kinase domains. (FIG. 1).

Figure 2:
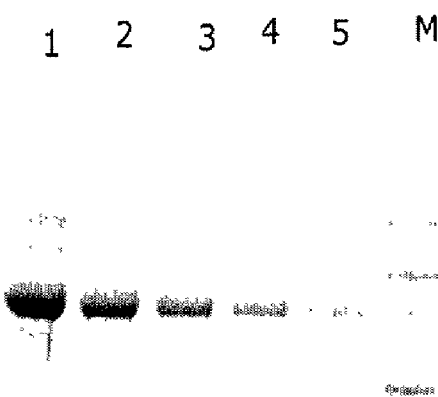
FIG. 2: Purified Rat VEGF-R2 Kinase Domain

A fusion protein was created consisting of the intracellular domain of the rat VEGF-R2 with a polyhistidine (HIS) tag added at the N-terminus by subcloning the above KpnI+NotI fragment into the pFastBac expression vector (Gibco/BRL, Grand Island, N.Y.) in frame with an artificial start codon followed by six histidine residues. Soluble recombinant kinase domain fusion protein of the rat VEGF-R2 was expressed in Hi5 insect cells using the baculovirus expression vector pFastBac (Gibco/BRL) and purified to greater than 85% homogeneity using metal chelate affinity chromatography essentially as described by the manufacturer (Cat. #69670 and Cat. #69755–3, Novagen, Madison, Wis.) (FIG. 2).

EXAMPLE 2

Screening Assay

A screening method was developed using the soluble rat VEGF receptor tyrosine kinase domain to phosphorylate a biotinylated peptide substrate for identification of compounds that inhibit the activity of the VEGF receptor. The PLC-1 peptide substrate consists of a fragment of phospholipase-C γ from amino acids 462 to 475 [(Biotin)KH-KKLAEGSAYEEV-Amide: SEQ.ID.NO.:3], a known in vivo substrate of the VEGF-R2, or alternatively, 0.6 micrograms of the artificial substrate poly Glu:Tyr (4:1) (Cat. #P-0275, Sigma, St. Louis, Mo.) which was randomly biotinylated.

Figure 4:
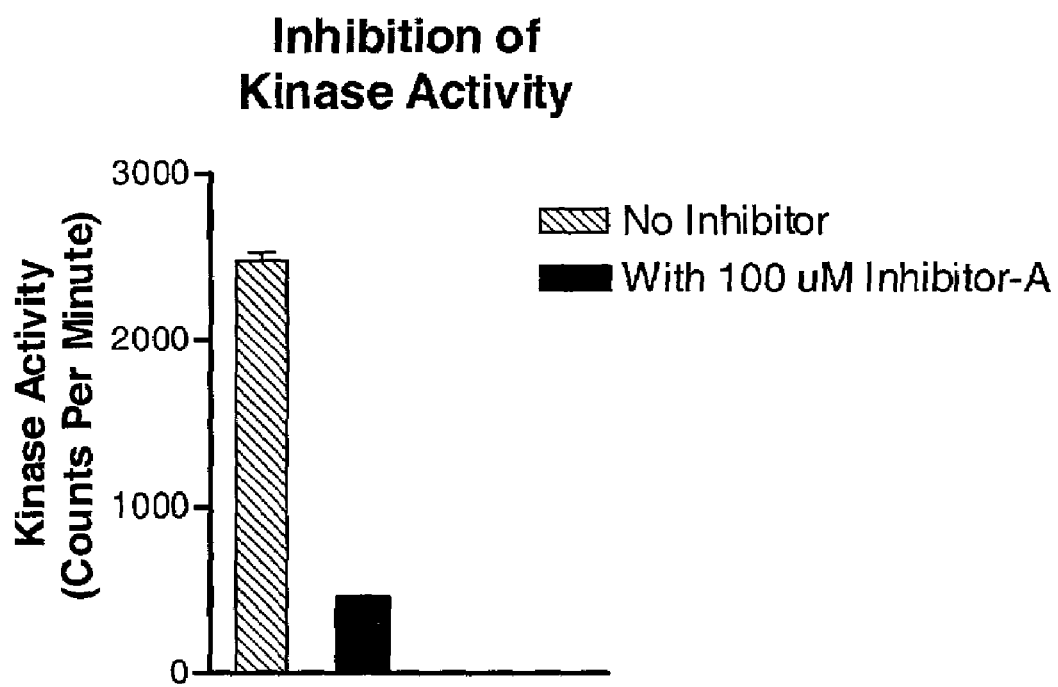
FIG. 4: Bar graph of Assay counts per minute +/− an inhibitor

A kinase reaction mixture was prepared containing 50 mM Tris-HCl pH=8, 10 mM $MgCl_2$, 0.1 mM $Na_3PO_4$, 1 mM DTT, 10 μM ATP, 0.25 μM biotinylated PLC-1 peptide substrate, and 0.8 μCuries per well $^{33}$P-γ-ATP [2000–3000 Ci/mmol]. 70 μl of the kinase reaction mixture was dispensed into the well of a streptavidin coated FlashPlate™ (Cat. #SMP-103, NEN, Boston, Mass.). Then 1 μl of test compound stock in 100% DMSO was added to the wells resulting in a final concentration of 1% DMSO in the reaction (100 μl final reaction volume includes subsequent enzyme solution). Then soluble rat VEGF receptor tyrosine kinase was diluted in 50 mM Tris-HCl pH=8.0, 0.1% BSA at a concentration of 5 ng per microliter and 30 μl (150 ng per test well) were added to each well to initiate the reaction. The reaction was incubated for one hour at 30° C. At the end of the 1-hour incubation, the reaction was terminated by aspirating the reaction mixture from the plate and washing the wells twice with PBS containing 100 mM EDTA. The biotinylated substrate remained immobilized on the Flashplate™ and the incorporation of $^{33}$P-γ-ATP is measured by reading the plate on a scintillation counter. Inhibition of the activity of the VEGF-R2 was measured by observing a reduced amount of $^{33}$P-γ-ATP incorporated into the immobilized substrate. As shown in FIG. 4, the $^{33}$P-γ-ATP incorporation into the immobilized substrate yielded a substantial difference compared to maximum inhibition with a known inhibitor (approximately a 5-fold difference). Thus this assay is useful as a high throughput-screening assay, where a 5–10 fold signal to noise (S/N) ratio is preferred as in terms of being economical (in terms of reagent usage), robust (clear delineation between a positive and negative result), and sensitive (detecting compounds that inhibit kinase activity at a useful concentration range). Signal to noise is defined as the (enzyme activity/enzyme activity in the presence of excess inhibitor).

Figure 5:
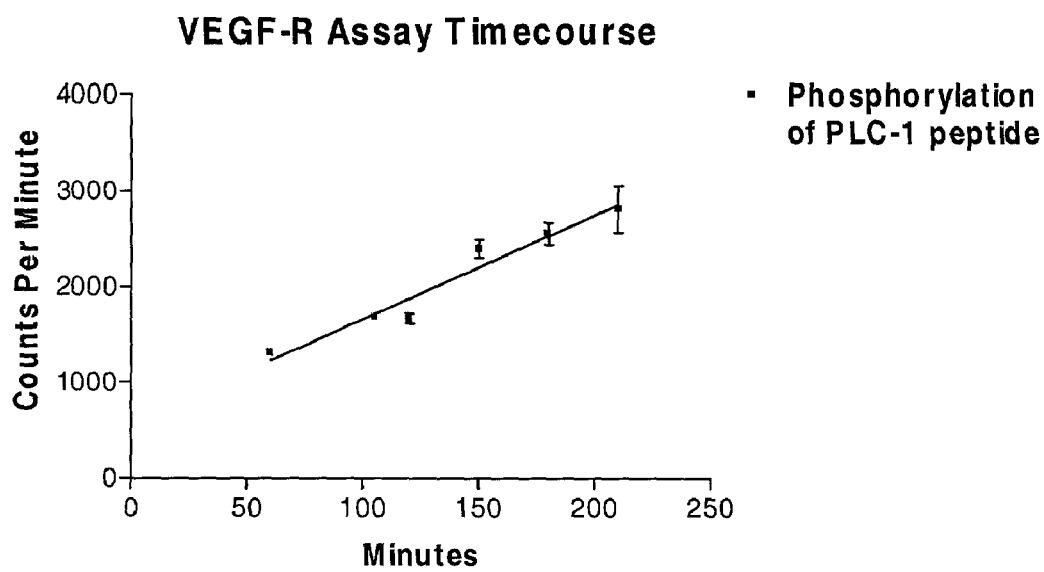
FIG. 5: Shows the linearity of the assay

To further evaluate the robustness of this assay, the conditions were replicated essentially as described to evaluate linearity of the kinase activity versus time. As shown in FIG. 5, the assay is linear for at least 3.5 hours. Thus this is useful when conducting high throughput screening to allow flexibility and confidence in assay performance.

Figure 3:
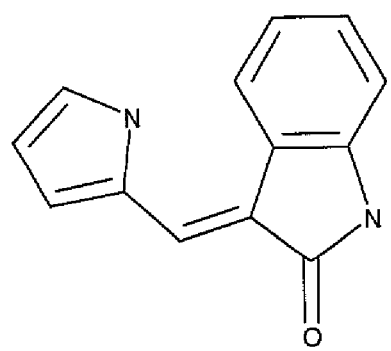
FIG. 3: IC50 of a rat VEGF-R2 inhibitor
Figure 3:
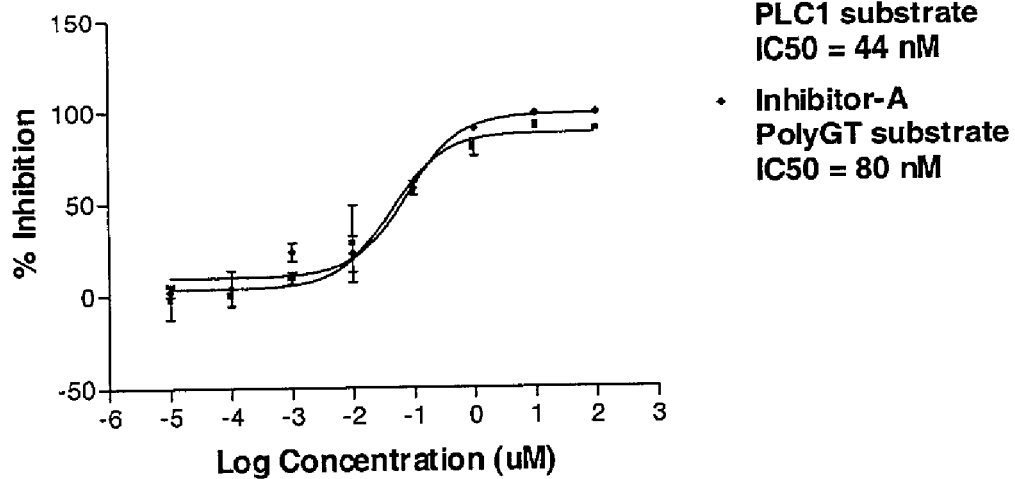

This assay was used to determine the IC50 for compounds that inhibit the kinase activity of the VEGF-R2 such as Inhibitor-A ($C_{13}H_{10}N_2O$, Cat. #CD00870, Maybridge Chemicals, Cornwall, UK) (FIG. 3). Test compounds were assayed in duplicate at 8 concentrations [100 μM, 10 μM, 100 nM, 10 nM, 1 nM, 100 pM, 10 pM]. A maximum and minimum signal for the assay was determined on each plate. The $IC_{50}$ (concentration of compound resulting in a 50 percent inhibition of the maximum signal) was calculated from the dose response curve of the percent inhibition of the maximum signal in the assay according to the formula [max signal–background/test compound signal–background (100)=% inhibition] by graphing the percent inhibition against the log concentration of test compound.

As shown in FIG. 3, inhibitor A successfully inhibits rat VEGF-R2 kinase activity, tested against the PLC1 substrate and the polyglutamate/tyrosine (Glu:Tyr 4:1) substrate.

EXAMPLE 3

Autophosphorylation Screening Assay

Screening Assay

A kinase reaction mixture is prepared containing 50 mM Tris-HCl pH=8, 10 mM $MgCl_2$, 0.1 mM $Na_3PO_4$, 1 mM DTT, 10 μM ATP, and 0.8 μCuries per well $^{33}$P-γ-ATP [2000–3000 Ci/mmol]. 70 μl of the kinase reaction mixture is dispensed into the well of an NTA-Nickel coated FlashPlate™ (Cat. #SMP107, NEN, Boston, Mass.). Then 1 μl of test compound stock in 100% DMSO was added to the wells resulting in a final concentration of 1% DMSO in the reaction (100 μl final reaction volume includes subsequent enzyme solution). Then soluble rat tyrosine kinase containing an N-terminal 6XHIS tag is diluted in 50 mM Tris-HCl pH=8.0, 0.1% BSA at a concentration of 5 ng per microliter and 30 μl (150 ng per test well) is added to each well to initiate the reaction. The reaction is incubated for one hour at 30° C. At the end of the 1-hour incubation, the reaction is terminated by aspirating the reaction mixture from the plate and washing the wells twice with PBS containing 100 mM EDTA. The 6XHIS-VEGF receptor becomes immobilized on the Flashplate™ and the incorporation of $^{33}$P-γ-ATP via autophosphorylation is measured by reading the plate on a scintillation counter. Inhibition of the enzymatic activity of the VEGF-R2 is measured by observing a reduced amount of $^{33}$P-γ-ATP incorporated into the immobilized enzyme. The results of this assay are shown in FIGS. 4 and 5.

What is claimed is:

1. A method to measure the effect of a putative VEGF-R2 kinase activity modulating compound comprising the steps, in order:
   A) providing a test compound, a rat VEGF-R2 kinase fusion protein (SEQ ID NO:4) comprising N-terminal hexahistidine linked to amino acids 786–1343 of the rat VEGF-R2 protein in a solution suitable to provide rat VEGF-R2 catalytic activity and containing $^{33}$P-γ-ATP as the source of phosphate;
   B) contacting the compound and the kinase fusion protein for sufficient time to provide a $^{33}$P phosphorylated substrate;
   C) isolating the phosphorylated kinase fusion protein by affinity capture using a multiwell assay plate;
   D) removing remaining $^{33}$P-γ-ATP by first aspirating the aqueous solution and then washing the plate with a phosphate buffered saline solution containing a divalent cation chelator in a concentration of about 1 mM to 100 mM; and
   E) detecting a change in kinase activity by monitoring the rate or absolute amount of $^{33}$P transfer to the kinase fusion protein by autophosphorylation in the presence of the compound.

2. A method to measure the effect of a putative VEGF-R2 kinase activity modulating compound comprising the steps, in order:
   A) providing a test compound, a rat VEGF-R2 kinase fusion protein (SEQ ID NO:4) comprising amino acids 786–1343 of the rat VEGF-R2 protein, and a biotinylated rat VEGF-R2 substrate in a solution suitable to provide rat VEGF-R2 catalytic activity and containing $^{33}$P-γ-ATP as the source of phosphate;
   B) contacting the compound, kinase fusion protein, and substrate for sufficient time to provide a $^{33}$P phosphorylated substrate;
   C) isolating the phosphorylated substrate by affinity capture using an avidin or streptavidin coated multiwell assay plate;
   D) removing remaining 33P-γ-ATP by first aspirating the aqueous solution and then washing the plate with a phosphate buffered saline solution containing a divalent cation chelator in a concentration of about 1 mM to 100 mM; and
   E) detecting a change in kinase activity by monitoring the rate or absolute amount of $^{33}$P transfer to the substrate in the presence of the compound.

* * * * *